US006183431B1

(12) United States Patent
Gach, Jr.

(10) Patent No.: US 6,183,431 B1
(45) Date of Patent: Feb. 6, 2001

(54) METATARSAL FRACTURE NEUTRALIZER

(76) Inventor: Richard E. Gach, Jr., 7180 SW. 9th St., Pembroke Pines, FL (US) 33023

( * ) Notice: Under 35 U.S.C. 154(b), the term of this patent shall be extended for 0 days.

(21) Appl. No.: 09/144,216

(22) Filed: Aug. 31, 1998

(51) Int. Cl.[7] ............................... A61F 13/00; A61F 5/37
(52) U.S. Cl. ............................... 602/23; 602/12; 128/882
(58) Field of Search ............................... 602/5, 6, 10–12, 602/15, 23, 27–30, 60–62, 65; 128/882, 893, 894; 5/648, 650, 651, 640, 630

(56) References Cited

U.S. PATENT DOCUMENTS

| 1,785,185 | 12/1930 | Day | 602/30 |
|---|---|---|---|
| 4,616,639 | 10/1986 | Huber | 128/99.1 |
| 5,007,416 | 4/1991 | Burns et al. | 602/27 |
| 5,197,942 | 3/1993 | Brady | 602/23 X |
| 5,528,784 | 6/1996 | Painter | 6/640 |

*Primary Examiner*—John Mulcahy
*Assistant Examiner*—Denise Pothier
(74) *Attorney, Agent, or Firm*—Malloy & Malloy, P.A.

(57) ABSTRACT

A metatarsal fracture neutralizer including a pair of brace elements secured with one another in sandwiching relation about a foot containing a fractured metatarsal, and a plurality of neutralization pads secured to the brace elements in confronting relation with one another. Two of the neutralization pads engage and immobilize the fractured metatarsal and the remaining neutralization pads engage and immobilize the remaining metatarsals so as to prevent movement of the fractured metatarsal due to muscle interconnection between metatarsals, while also permitting a full range of motion at the ankle joint connected to the metatarsals in order to aid comprehensive rehabilitation of the foot. The fracture neutralizer further includes three compression pads operatively coupled with the neutralization pad that engages the fractured metatarsal, a first compression pad being disposed to engage a first side of the fractured metatarsal at a fracture site, and the remaining compression pads engaging a second side of the fractured metatarsal opposite the first side at points distal and proximal to the fracture site. Furthermore, the first compression pad pushes the fractured metatarsal in a direction which opposes a direction of the fracture and which opposes a direction in which the remaining compression pads push, thereby maintaining the fractured metatarsal in a proper healing orientation, upon securement of the brace elements about the foot.

21 Claims, 2 Drawing Sheets

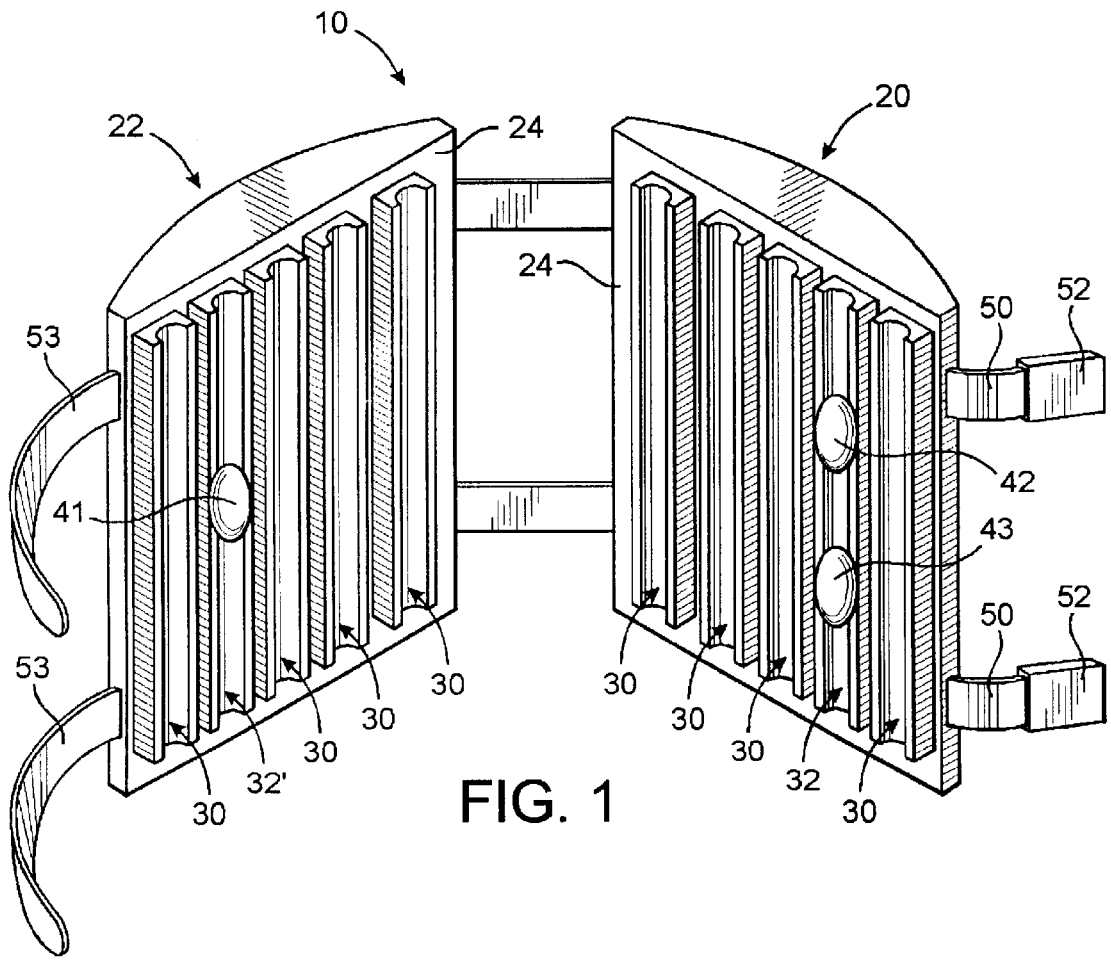
FIG. 1
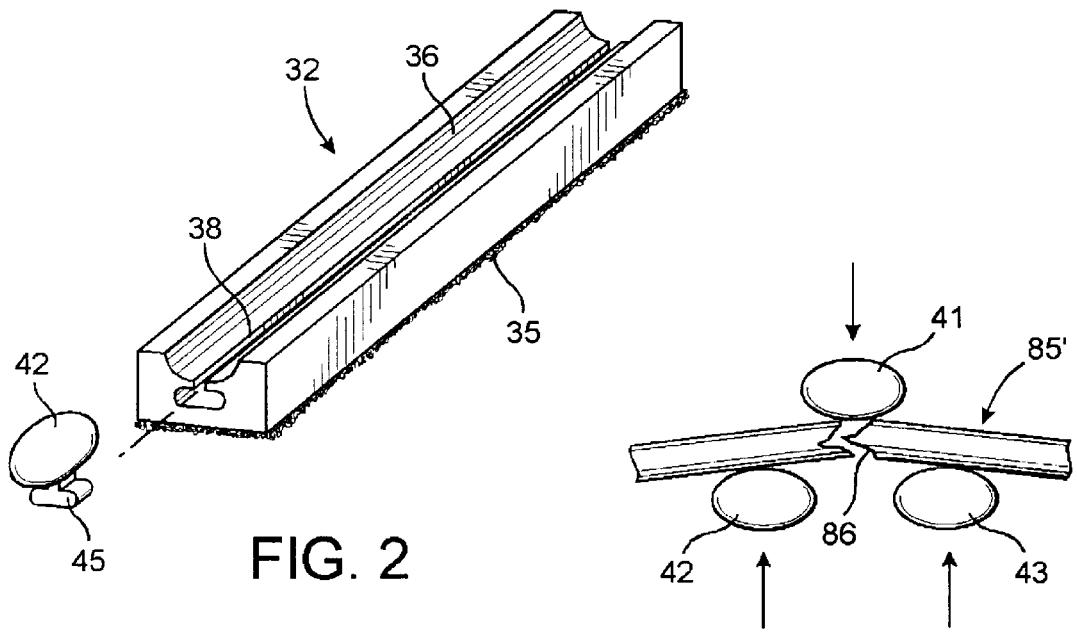
FIG. 2
FIG. 3

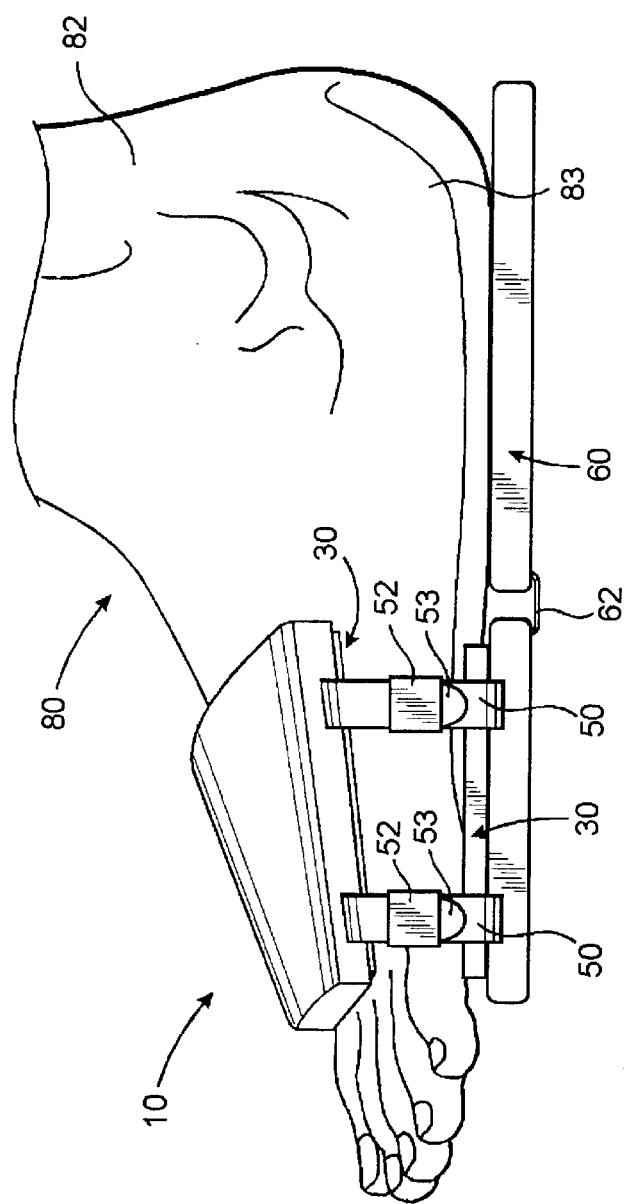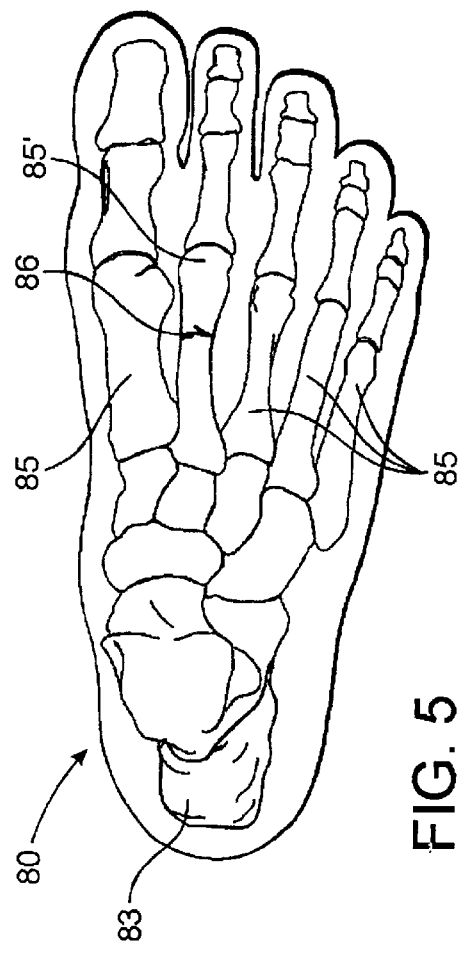
FIG. 4
FIG. 5

METATARSAL FRACTURE NEUTRALIZER

BACKGROUND OF THE INVENTION

1. Field of the Invention

The present invention relates to a metatarsal fracture neutralizer to be worn principally on a patient's foot after the occurrence of a metatarsal fracture, in order to effectively immobilize and isolate the fractured metatarsal, thereby promoting healing thereof, while also permitting adjustability and adaptability, such as to accommodate for reductions in swelling, and also permits a substantial range of motion to be maintained with other associated joints, thereby minimizing joint atrophy and/or stiffness which can often lead to extended rehabilitation requirements.

2. Description of the Related Art

Limb extremities of the human body, such as the hand and foot, typically include a series of elongated, longitudinal bones, namely the metacarpal and metatarsal bones, which run along a length thereof and generally define a primary structure of that limb extremity. These longitudinal bones, however, are generally not substantially thick in diameter, and as a result of the substantial use and impact to which the limit extremities are subjected, can often be susceptible to fractures. Whether these fractures include a complete break or the more typical partial break, the only true rehabilitation remedy involves a prolonged period of isolation and immobilization so as to promote internal healing of the bone. Naturally, if the bone is not completely immobilized and maintained in a proper healing orientation throughout the healing process, a likelihood that the bone will heal into an improper orientation can result. As a result, a variety of systems and methods have been developed so as to secure and maintain the fractured longitudinal bone in a proper healing orientation for an extended period of time.

The typical rehabilitation aid utilized to heal conventional fractures is a cast placed on the limb extremity. Typically, such immobilizing casts are formed of plaster and function to immobilize the longitudinal bone as well as a remainder of the limb extremity. For example, in the circumstance of a metatarsal fracture, the cast typically extends completely about the foot, leaving only the patient's toes exposed, and extends over the leg and at least partially up the ankle, thereby completely immobilizing the foot containing the fracture. This typical cast is then maintained on the foot for an extended period of time so as to permit the properly set metatarsal contained within the cast to heal substantially. Indeed, the healing period is often quite extensive, the only relief from the cast coming after a pre-determined period of time when doctors typically remove an original cast so as to examine the progress of the healing, and then place a new cast on the foot.

Once the prescribed period of time within the cast has been met, the typical plaster cast is then removed from the patient's foot and an air cast or like shock absorbent system is placed on the foot so as to provide protection. This permits the doctor or other medical personnel to properly examine the bone which has been fractured and thereby ensure that complete healing is occurring. Often times, however, because of the nature of the immobilization achieved by conventional casts and braces, although rehabilitation of the bone itself may be completed once the fracture has been fully repaired, the overall rehabilitation process is far from over. In particular, because the entire foot has generally been immobilized so as to heal the metatarsal fracture, the other joints and portions of the foot may become atrophied or otherwise stiffened. A typical example is at the ankle joint wherein a lack of movement can cause a tissue build up therein which severely limits the range of motion for the ankle until a patient can rehabilitate for an extended period of time, gradually increasing their range of motion until the full range is once again achieved. Unfortunately, however, this can be a time consuming and often a difficult and painful process in order to rehabilitate a condition which is merely a side affect of the treatment of a bone fracture.

Along these lines, it would be highly beneficial to provide an improved metatarsal fracture neutralizer which can secure and maintain a fractured metatarsal, which has been set into a proper healing orientation, in that orientation for an extended period of time, yet which will permit remaining joints and portions of the foot to maintain a substantially free range of motion so as to minimize additional rehabilitation that is required once the fracture itself is healed. Moreover, such a system should be capable of accommodating for variations in the size and dimension of the foot itself, as typically result from swelling. For example, when the fracture initially takes place the foot is naturally substantially swollen and as a result has an increased diameter. Although it is ideal to place a permanent cast on the foot as quickly as possible, physicians are often reluctant to do so or must put on an initial cast with the knowledge that they must replace that cast in due time due to the fact that the swelling will naturally reduce after some time has past. Specifically, a secure and snug fitting cast when the foot is swollen will naturally be substantially loose fitting and can make the fracture subject to further displacement once the swelling goes down. As a result, it would be beneficial to provide a metatarsal fracture neutralizer which is capable of being continuously adjusted so as to maintain its secure fracture immobilizing fit around the foot and about the metatarsal containing the fracture.

It is noted that others in the art have attempted to devise braces and the like which specifically isolate on a bone fracture for healing purposes. It is noted, however, that such devices still do not provide a uniform compression of the longitudinal bone and in particular, the dorsum and plantar aspects of the patient's foot. Moreover, such devices may be primarily beneficial for later stages of rehabilitation, as they do not take into account the close proximately and muscle interconnection between adjacent metatarsals which can result in movement or displacement of even the most securely held fractured metatarsal if appropriate accommodations are not made.

Lastly, it is noted that one primary benefit to a plaster cast is its general adjustability to conform to different configurations encompassing a variety of foot sizes and shapes, thereby permitting it to be easily adjustable to fit any size patient or any fracture site of the patient. As a result, an improved metatarsal fracture neutralizer should also be structured to accommodate for varying spaces between metatarsals as well as varying sized feet. Additionally, such a device should permit weight to be born by the foot in some limited circumstances, thereby preventing muscle deterioration of the foot during the rehabilitation process. Indeed, such weight bearing capability is achieved in conjunction with the maintenance of the free range of motion of the various joints, thereby isolating the overall rehabilitation to the metatarsal and associated longitudinal bones which could impact or misorient the fractured metatarsal.

SUMMARY OF THE INVENTION

The present invention relates to a metatarsal fracture neutralizer. In particular, the metatarsal fracture neutralizer includes a first and second brace elements which are positioned in sandwiched relation about a foot containing the fractured metatarsal. The first and second brace elements are preferably adjustably secured with one another, thereby adjusting the spacing therebetween for accommodating for feet of varying thicknesses and/or for varying pressures to be exerted on the foot.

Additionally, the metatarsal fracture neutralizer of the present invention includes a plurality of neutralization pads. These neutralization pads are structured to be secured with the first and second brace elements, preferably in an adjustable fashion and in generally confronting relation with one another on the corresponding first and second brace elements. Along these lines, upon the first and second brace elements being secured in the sandwiched relation about the foot containing the fractured metatarsal, at least two of the neutralization pads engage the fractured metatarsal in substantially sandwiching and immobilizing relation. Furthermore, additional neutralization pads are preferably provided and thereby generally engage and immobilize at least a second metatarsal that is disposed adjacent to the fractured metatarsal, and in a most preferred embodiment all of the metatarsals contained within the foot. As a result, movement and mis-orientation of the fractured metatarsal as a result of muscle interconnection between all of the adjacent metatarsals of the foot is prevented. Moreover, it is noted that the neutralization pads run substantially along a length of each metatarsal which they engage, however, they are structured and disposed to still permit a substantial range of motion at the joints connected to the metatarsals of the foot, thereby substantially aiding comprehensive rehabilitation of the foot and minimizing the need for additional rehabilitative time for non-fracture related deterioration of the foot.

Operatively coupled with the neutralization pads that engage the fractured metatarsal are at least two compression pads. These compression pads are adjustably positioned along a length of neutralization pads so as to be properly aligned to correspond with a fracture site of the fractured metatarsal. In particular, at least one of the compression pads is disposed to engage a first side of the fractured metatarsal generally at the fracture site, while at least another of the compression pads engages the second side of the fractured metatarsal opposite to the first side. Preferably, the opposing compression pad disposed on the second side of the fractured metatarsal includes two engagement points, one distal and another proximal to the fracture site. Accordingly, it is noted that the compression pad that engages the first side of the fractured metatarsal and is disposed directly at the fracture site is structured to push the fractured metatarsal in a direction which opposes a direction of the fracture when the first and second brace elements are tightened around the foot. Naturally, the opposing compression pads which are disposed distal and proximal to the fractured site oppose the pushing direction of the compression pad at the fracture site and the fractured metatarsal is accordingly urged and maintained in an aligned, proper healing orientation.

It is an object of the present invention to provide a metatarsal fracture neutralizer capable of isolating a fracture in a metatarsal and immobilizing it so as to promote proper healing thereof without contributing to joint atrophy.

A further object of the present invention is to provide a metatarsal fracture neutralizer which isolates metatarsals adjacent to a fractured metatarsal thereby limiting and preventing fracture mis-orientation as a result of muscle interconnection between adjacent metatarsals.

Another object of the present invention is to provide a metatarsal fracture neutralizer which is adaptable for use with a variety of different size feet and bone configurations.

An additional object of the present invention is to provide a metatarsal fracture neutralizer capable of effectively neutralizing and securing multiple fractures, and which is adjustable so as to provide concentrated pressure directly at the site of each fracture.

Also another object of the present invention is to provide a metatarsal fracture neutralizer which permits some weight to be born by a foot containing a fracture, without permitting excessive weight that could lead to complications to the healing process.

Still another object of the present invention is to provide a metatarsal fracture neutralizer which can be easily removed and repositioned so as to permit convenient adjustability and minimize the potential formation of skin sores at the area of skin surrounding the fracture.

Another object of the present invention is to provide a metatarsal fracture neutralizer capable of being easily and effectively adjusted to provide substantial pressure at the fracture site during various stages of swelling at the fracture site.

Also another object of the present invention is to provide a metatarsal fracture neutralizer capable of permitting a doctor more access to examination of a fractured area at any stage of rehabilitation.

An object of the present invention is to provide a limb extremity fracture neutralizer capable of isolating and immobilizing a fracture at a limb extremity, such as a hand or foot, while maintaining a range of motion at adjacent joints, thereby promoting substantial healing without increasing rehabilitation time due to the immobilization of the joints.

These and other objects will become apparent in further view of the detailed description and accompanying claims.

BRIEF DESCRIPTION OF THE DRAWINGS

For a fuller understanding of the nature of the present invention, reference should be had to the following detailed description taken in connection with the accompanying drawings in which:

FIG. 1 is a perspective view of the preferred metatarsal fracture neutralizer of the present invention;

FIG. 2 is an isolated perspective view of the neutralizer pad and compression pad utilized with the fracture neutralizer of the present invention;

FIG. 3 is schematic illustration of the engagement of the compression pads at the fracture site of the bone;

FIG. 4 is a side view of the fracture neutralizer of the present invention in use on a foot containing a fractured metatarsal; and FIG. 5 is a skeletal representation of a foot depicted so as to illustrate a normal positioning and spacing of metatarsals in the skeletal make up of a foot.

Like reference numerals refer to like parts throughout the several views of the drawings.

DETAILED DESCRIPTION OF THE PREFERRED EMBODIMENT

Shown throughout the Figures, the present invention is directed towards a metatarsal fracture neutralizer, generally indicated as 10. In particular, the fracture neutralizer of the present invention is structured so as to immobilize and isolate a fracture within a longitudinal bone of a limb extremity, and in the preferred embodiment isolates a fracture within at least one metatarsal 85 of a foot 80.

Specifically, the metatarsal 85 of a foot 80, as with all longitudinal bones in limb extremities, typically extend in the forward region of the foot 80, as illustrated in FIG. 5, and are interconnected between the skeletal structure that defines the toes and the heel and ankle. As a result, a variety of joints interconnect the metatarsals 85 with the remaining skeletal structure of the foot 80.

In the preferred embodiment, the metatarsal fracture neutralizer 10 includes a first brace element 20 and a second brace element 22. The brace elements 20 and 22 preferably provide a generally rigid, elongate, rectangular configuration conforming to an average size width of a foot 80 and having a sufficient length to generally overlap the metatarsal region of most feet 80. Moreover, the brace elements 20 and 22 are structured to be disposed in sandwiching relation about a foot 80 wherein at least one fractured metatarsal 85' is contained, as best seen in FIG. 4. The generally rigid nature of the brace elements 20 and 22 provides a stiff structure against which the brace elements 20 and 22 may be secured with one another.

The fracture neutralizer 10 of the present invention preferably includes a fastener assembly that is specifically structured so as to secure the first and second brace elements 20 and 22 with one another and at variable spacing from one another. In particular, as best illustrated in FIG. 4, the generally rigid construction of the brace elements 20 and 22 are disposed on opposite upper and lower sides of the foot 80. Typically, however, shortly after a fracture is suffered, a substantial degree of swelling is exhibited by the foot 80 in the area of the fracture. As a result, when the fracture neutralizer 10 is first put on the foot 80, a secure and tight engagement of the brace elements 20 and 22 with one another has an increased spacing than will be required as the swelling decreases. Unlike conventional braces and casts, the fracture neutralizer 10 of the present invention is able to be adjusted, such as by reduction of that variable spacing between the first and second brace elements 20 and 22, so as to accommodate for the reduction in swelling and still maintain the effective engagement and isolation of the metatarsals 85 of the foot 80 by the same assembly. In the preferred embodiment of the Figures, the fastener assembly includes a pair of generally elongate straps 50. These straps 50 may be formed of any of a variety of flexible or semi-flexible materials and may comprise one continuous strap or a plurality of strap segments. Preferably the straps 50 each include a buckle or clip type fastener end 52 as well as a free end 53. Utilizing a conventional structure, and preferably a ratcheting type structure so as to facilitate progressive tightening, the free end 53 of the strap 50 extend into the fastener end 52 until a desired fastening is achieved. In another instance, the straps 50 are preferably disposed so as to ensure that the first and second brace elements 20 and 22 are generally parallel with another and/or substantially conform to the plane of the portion of the foot 80 which they engage, thereby maintaining uniform pressure and engagement with the metatarsals 85 of the foot 80 upon tightening. Of course, it is understood that a variety of different structures could be utilized to define the faster assembly, and that fewer or additional straps 50 may also be incorporate as deemed appropriate. Also, it is noted that the fastener assembly which permits the progressive tightening of the first and second brace elements 20 and 22 about the foot 80 also permit the facilitated removal and re-positioning of the fracture neutralizer 10. This is particularly beneficial when subsequent medical examination is required, or if a patient is permitted to remove the neutralizer at times during rehabilitation.

Secured on the confronting faces 24 of each of the brace elements 20 and 22 are at least two neutralization pads 32 and 32'. In particular, these two neutralization pads 32 and 32' are structured to be adjustably secured to the confronting faces 24 of the brace elements 20 and 22 in a generally aligned relation with the fractured metatarsal 85'. The two neutralization pads 32 and 32' are structured to be disposed in generally confronting relation with one another so as to engage and immobilize the fractured metatarsal 85' with which they are aligned. As a result, the neutralization pads 32 and 32' generally retain the fractured metatarsal 85' in sandwiched relation therebetween such that upon tightening of the fastener assembly, and accordingly reducing the spacing between the brace elements 20 and 22 about the foot 80, the neutralization pads 32 and 32' will become increasingly engaged about the fractured metatarsal 85'. To this end, each of the neutralization pads 32 and 32' is preferably generally elongate, extending substantially along an entire length of the fractured metatarsal 85'. Indeed, this generally elongated engagement with the fractured metatarsal 85' ensures a more secure engagement and immobilization with the entire fractured metatarsal 85' so as to further isolate and restrict movement at the fracture site 86. Still, however, it is noted that the neutralization pads 32 and 32', as well as the brace elements 20 and 22, while being generally elongate so as to extend substantially along an entire length of the fractured metatarsal 85', is preferably not so long as to restrict movement at other joints. As mentioned, often a substantial drawback associated with fracture rehabilitation is the fact that known cast-type devices typically immobilize all of the joints adjacent to the fractured metatarsal 85', such as at the ankle 82 or even at the toes. As a result, after a prolonged period of use of the conventional cast, the joints become stiff and the range of motion therein is substantially decreased leading to the requirements of substantially extensive rehabilitation merely to regain the range of motion in those adjacent joints. The fracture neutralizer 10 of the present invention is structured such that even when the neutralization pads 32 and 32' engage substantially along the entire length of the fractured metatarsal 85', movement of the ankle joint is permitted, as well as movement of other joints which engage the fractured metatarsal 85'. In this manner, part of the rehabilitation process can include a routine of stretching or flexing of those joints in order to maintain their normal range of motion and eliminate the need for the additional rehabilitation steps. Also, a series of aquatic exercises can also be incorporated into the rehabilitation process, and indeed, the present invention is preferably generally water resistant such that it may be worn during some aquatic exercises.

Looking specifically to the preferred structure of the neutralization pads 32 and 32', as indicated, each is preferably elongate, but also includes an elongate trough 36 therein. The elongate trough 36 is specifically sized so as to generally receive and retain the fractured metatarsal 85' therein, thereby providing a secure sandwiching engagement about the fractured metatarsal and generally preventing lateral movement between the fractured metatarsal 85' and the neutralization pads 32 and 32'. Moreover, an underside 35 of the neutralization pads 32 and 32' preferably include structure to permit adjustable securement to the confronting faces 24 of the first and second brace elements 20 and 22. In the preferred embodiment, hook and loop fastener had are preferably disposed on the under surface 35 of the neutralization pads 32 and 32', as well as the confronting faces 24 of the first and second brace elements 20 and 22. As a result, the neutralization pads 32 and 32' can be specifically aligned and oriented to correspond to the position and orientation of the fractured metatarsal 85' on any foot. Such adjustable configuration is particularly beneficial so as to permit a stock fracture neutralizer 10 to be provided, with the physician or other practitioner configuring the positioning of the neutralization pads 32 and 32' to correspond the position and orientation of the fractured metatarsal 85' in the actual patient's foot 80.

Although only two neutralization pads 32 and 32' are actually required so as to sandwich the fractured metatarsal 85', in a preferred embodiment, a plurality of additional neutralization pads 30 are also provided. In particular, these additional neutralization pads 30 all preferably include substantially similar and interchangeable structures, and may indeed be utilized in circumstances wherein more than one fractured metatarsal 85' is present in the foot 80. For example, the additional neutralization pads 30 are also preferably generally elongate, with some potentially being slightly shorter than others to accommodate for the shorter metatarsals within the normal skeletal structure of the foot 80, however, they are preferably adjustably secured to the confronting faces 24 of the first and second brace elements 20 and 22. As a result, the practitioner is able to adjustably position all of the neutralization pads 30 in properly aligned relation with the additional metatarsals 85 of the foot 80. As indicated, the additional neutralization pads 30 can be utilized so as to engage and immobilize an additional fractured metatarsal 85'. However, in the preferred embodiment a plurality of the neutralization pads 30, 32, and 32' will always be utilized, a pair of confronting neutralization pads being adjustably positioned and disposed so as to engage each metatarsal 85 of the foot 80, including the fractured metatarsal 85'. Such secure engagement and immobilization of all of the metatarsals 85, and especially at least those metatarsals 85 that are directly adjacent to the fractured metatarsal 85', is particularly beneficial because of the typical muscle interconnection between all of the metatarsals 85 in the foot 80. Specifically, the skeletal structure of the foot 80 provides for five distinct metatarsals 85, however, the muscle interconnection and disposition thereover provides that in many circumstances the movement resulting from inadequate immobilization of adjacent or other metatarsals 85 within the foot 80 can result in an internal pulling or a repositioning of the fractured metatarsal 85', even if it is generally immobilized. For example, this repositioning in addition to being in the form of a separation of the fractured metatarsal 85' at the fracture site 86 can also include a twisting or misalignment of the segments at the fracture site 86 from one another, all of which can lead to improper healing. As a result, it is preferred to have a plurality of neutralization pads, each engaging one of the metatarsals 85 of the foot 80 in a manner which still permits the full range of motion with the adjacent joints, but which engages and neutralizes each metatarsal 85 so as to prevent movement or mis-orientation of the fractured metatarsal 85'.

The fracture neutralizer 10 of the present invention further includes at least two, but preferably three compression pads 41, 42, and 43. The compression pads 41, 42 and 43 are structured to be operatively coupled with at least the neutralization pads 32 and 32' which engage the fractured metatarsal 85'. In particular, the compression pads 41, 42, and 43 are preferably formed of a generally stiff, high density padding or foam material and are preferably structured to be adjustably positionable along a length of the neutralization pads 32 and 32'. The compression pads 41, 42, and 43 are structured to be oriented relative to the fracture site 86 of a fractured metatarsal 85' which is engaged by the neutralization pads 32 and 32'. In an alternative embodiment, fixed positioning of the compression pads 41, 42, and 43 on the neutralization pads 32 and 32' may be utilized, with specific predefined structures which correspond the location of the fracture site within the fractured metatarsal 85' being selected for use. In the preferred embodiment, however, the compression pads 41, 42, and 43 are adjustably secured to the neutralization pads 32 and 32' such that a practitioner may specifically position the compression pads 41, 42, and 43 to correspond the specific location of the fracture site 86 in the fractured metatarsal 85 to be neutralized. As illustrated in the Figures, a preferred method of adjustable positioning includes a mating structure defined on the compression pads 41, 42, and 43 and the neutralization pads 32 and 32'. In the preferred embodiment, a generally elongate lock channel 38 is defined in the trough 36 of each neutralization pad, as best illustrated in FIG. 2. A corresponding lock segment 45 extends from the corresponding compression pad, and is structured to slidably enter the lock channel 38. Preferably, the compression pads 41, 42 and 43 include a generally oval or circular shape such that when in one orientation they may slide freely within the trough 36, with the lock segment 45 riding within the lock channel 38. When the compression pad is positioned in a desired location relative to the fractured site 86, the compression pad is preferably locked in place. In the illustrated embodiment, the general shape of the compression pad is such that it rides within the trough 36 into an appropriate position, when in one orientation, and upon turning or rotating of the compression pad it becomes locked in place, such as by an abutment of the compression pad along the upper lips of the trough 36 of the neutralization pad 32. Indeed, it is noted that in the preferred embodiment the compression pads 41, 42, and 43 will generally protrude from the trough, or at least partially fill an area of the trough at the vicinity of the fracture site 86.

As indicated, preferably three compression pads 41, 42, and 43 are utilized at each fractured site 86. A first of the compression pads 41, as best seen in FIG. 3, is structured to engage a first side of the fractured metatarsal 85', preferably directly at the fracture site 86. In particular, the first compression pads 41 is preferably positioned on a first side of the fractured metatarsal 85' such that when the fracture neutralizer 10 is securely tightened about the foot 80, the first compression pad 41 pushes the fractured metatarsal 85' in a direction that is generally opposite a direction of the fracture 86. As illustrated in FIG. 3, fractures typically will occur towards a top or a bottom of a foot 80. As a result, in order to effectuate proper alignment of the fractured metatarsal 85', the fracture site 86 is preferably pushed in a direction opposite the direction of that fracture, thereby positioning and maintaining the fractured metatarsal 85' in a proper healing orientation. Indeed, even though a practitioner would typically align and position the fractured metatarsal 85' manually prior to utilizing the fracture neutralizer 10, the tendency of the fractured metatarsal 85' is to return to the fracture position. As a result, the first compression pad 41 disposed directly at the fracture site 86 counters this general tendency. Additionally, the second and third compression pads 42 and 43 are structured to generally straddle the fracture site 86 of the fractured metatarsal 85'. Specifically, one compression pad 42 is disposed proximal to the fracture site 86 while the other compression pad 43 is disposed distal to the fracture site 86. As a result, it is seen that on one side the first compression pad 41 pushes in one direction, while the other compression pads 42 and 43 disposed on a second or opposite side generally oppose the direction of pushing of the first compression pad 41. This opposing engagement and immobilization of the fractured metatarsal 85' functions to substantially maintain proper alignment and orientation of the fractured metatarsal 85' at all times. Moreover, because the compression pads 41, 42, and 43 are disposed on the neutralization pads 32 and 32', additional pressure is exerted at the fracture site 86 such that increased immobilization and securement is achieved at the fracture site 86. From the preceding structure, it is noted that compression pads 42 and 43 which straddle the fracture site 86 may generally be formed into a single elongate compression pad having a pair of spaced apart protruding engagement points that actually engage the foot 80 at locations distal and proximal of the fracture site 86.

As previously indicated, the first and second brace elements 20 and 22 are structured to be adjustably secured about the foot 80, as illustrated in FIG. 4. This adjustable securement not only enables a patient or practitioner to continuously tighten the fracture immobilizer 10, as required in order to maintain proper engagement with the metatarsal 85, but also functions to effectively permit temporary removal of the fracture immobilizer 10. As indicated, the plurality of neutralization pads and compression pads are preferably adjustably oriented relative to the brace elements so as to particularly correspond the structure of a patient's foot 80 in a location of the fracture site 86. Upon removal of the fracture immobilizer 10, however, the positions and orientations of these components are maintained and a patient or practitioner can easily define a frame of reference on the foot so as to ensure proper repositioning when the fracture neutralizer 10 is to be repositioned on the patient's foot 80. By permitting removal of the fracture neutralizer 10 in a convenient fashion, however, additional rehabilitation of the patient can be achieved. In particular, although the preferred structure of a the fracture mobilizer 10 of the present invention is such that a substantially full range of motion is permitted with adjacent joints, in some circumstances it may be preferable to limit or otherwise restrict the range of motion at other joints, such as the ankle 82. In such circumstances, however, by permitting removability of the fracture neutralizer 10, a patient is able to exercise their foot 80 at various locations including the ankle joint. Moreover, a common occurrence when prolonged use of a brace or cast is necessitated relates to the potential formation of skin sores on the area that is constantly covered and engaged by the apparatus. The fracture neutralizer 10 of the present invention enables a patient, in some limited circumstances, to position their foot 80 in a safe and supported orientation, and to remove the fracture neutralizer 10 for an extended period of time so as to permit their foot 80 to breath. Additionally, when further examinations are required by a practitioner, and additionally x-rays or closer examination of the foot 80 is required, the practitioner can easily remove the fracture neutralizer 10 to perform these additional checks and procedures, and need not utilize or form a brand new fracture neutralizer as the rehabilitation process continues.

As indicated, in some instances it may be beneficial to limit the range of motion at certain joints such as the ankle 82 of the foot 80. Such a circumstance particularly arises when it is desirable to permit or limit the amount of weight to be born by the foot 80 containing the fracture. It is noted, that based upon the normal structure and arthrokinematics of a human foot 80, when a person desires to place weight on the forward or metatarsal region of the foot 80, that patient must necessarily flex their ankle 82, by pushing their toes away from the ankle 82. This is evidenced in a normal walking stride, wherein the orientation of the foot 80 must be extended relative to the ankle 82 when a step is completed and/or when a person wishes to push off the metatarsal region of the foot 80. As a result, the present invention includes a joint immobilization assembly coupled with at least one of the brace elements and structured to selectively limit a range of motion at the ankle 82 of the foot 80. In the preferred embodiment, the joint immobilization assembly includes an elongated rigid panel 60 that extends preferably from the brace element that is positioned on an undersurface of the foot 80. The elongate rigid panel 60 extends from the brace element into engaging relation with a heel 83 of the foot 80. Moreover, the elongate rigid panel 60 is preferable removably and adjustably coupled via a bracket 62 that extends into both the brace element as well as the elongate rigid panel 60. It is note that in the preferred embodiment, the bracket 62 is preferably structured to vary a range of motion, and as such, a ratcheting type structure wherein a certain degree of a flexibility of the rigid panel 60 relative to the brace element may be permitted depending upon the amount of weight which a practitioner determines can be or should be born by the front of the foot 80. In use, the elongate rigid panel 60 engages the heel 83 such that when an individual wishes to flex the metatarsal region of the foot 80 away from the ankle 82, the rigid panel 60 engages the heel 83 and resists further pivotal movement. As a result, a user is generally forced to walk on their heels 83 and the amount of weight or pressure that is placed on the metatarsals absent from dramatic and uncomfortable movement is limited. As a practitioner determines that additional weight can be born by the metatarsals, however, the degree of relative movement between the rigid panel 60 and the brace elements is increased so as to increase the amount of flexing that the foot 80 can tolerate beyond the strict 90 degree or less angle at the ankle 82.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A metatarsal fracture neutralizer comprising:
    a first brace element and a second brace element, said first and said second brace elements being adjustably secured with one another adapted to be in sandwiching relation about a foot containing at least one fractured metatarsal;
    at least two neutralization pads, said neutralization pads secured to said first and second brace elements in generally confronting relation with one another,
    said neutralization pads being structured to generally engage and immobilize the fractured metatarsal in sandwiched relation therebetween,
    said neutralization pads being structured and disposed to permit a substantial range of motion at joints connected to the fractured metatarsal, thereby substantially aiding comprehensive rehabilitation of the foot,
    at least three compression pads operatively coupled with at least said neutralization pads which are sized and configured to engage the fractured metatarsal,
    at least a first of said compression pads sized and configured to engage a first side of the fractured metatarsal generally at a fracture site,
    at least a second and a third of said compression pads being disposed in spaced apart relation from one another and being structured to engage a second side of the fractured metatarsal opposite said first side of the fractured metatarsal at points proximal and distal to the fracture site, and said first compression pad and said second and third compression pads structured to generally push against one another, and to thereby urge and maintain the fractured metatarsal in an aligned, proper healing orientation, upon securement of said first and second brace elements with one another about the foot.

2. A metatarsal fracture neutralizer as recited in claim 1 further comprising a fastener assembly securing said first and said second brace elements with one another at a variable spacing from one another so as to permit a reduction of said variable spacing and accordingly a tightening of said first and said second brace elements about the foot upon a reduction in swelling in the foot.

3. A metatarsal fracture neutralizer as recited in claim 1 wherein said neutralization pads are adjustably secured to said brace elements so as to facilitate proper alignment with the fractured metatarsal in feet of varying sizes and configurations.

4. A metatarsal fracture neutralizer as recited in claim 1 wherein said neutralization pads are sized and configured to extend along a substantial length of the fractured metatarsal so as to maintain effective engagement with and isolation of the fractured metatarsal.

5. A metatarsal fracture neutralizer as recited in claim 1 including a plurality of said neutralization pads, said neutralization pads being further structured to generally engage and immobilize at least a second metatarsal disposed adjacent fractured metatarsal so as to prevent movement of said fractured metatarsal as a result of muscle interconnection therebetween.

6. A metatarsal fracture neutralizer as recited in claim 5 wherein said neutralization pads are adjustably secured to said brace elements so as to facilitate proper alignment with the metatarsals regardless of an actual spacing therebetween.

7. A metatarsal fracture neutralizer as recited in claim 1 including a plurality of said neutralization pads, said neutralization pads being further structured to generally engage and immobilize each metatarsal of the foot so as to prevent movement of the fractured metatarsal as a result of muscle interconnection therebetween.

8. A metatarsal fracture neutralizer as recited in claim 1 further comprising at least two compression pads operatively coupled with at least said neutralization pads which are sized and configured to engage the fractured metatarsal, said compression pads being structured to engage the fractured metatarsal from opposite sides thereof at generally a fracture site thereof and being structured push against one another, and to thereby urge and maintain said fractured metatarsal in an aligned, proper healing orientation, upon securement of said first and second brace elements with one another about the foot.

9. A metatarsal fracture neutralizer as recited in claim 8 wherein said compression pads are adjustably secured to said neutralization pads so as to permit proper alignment thereof with a fracture site on the fractured metatarsal.

10. A metatarsal fracture neutralizer as recited in claim 8 wherein one of said compression pads is sized and configured to be disposed directly at said fracture site, and another of said compression pads is structured to engage the fractured metatarsal at points proximal and distal to said fracture site.

11. A metatarsal fracture neutralizer as recited in claim 8 comprising at least three of said compression pads adjustably and operatively coupled with at least said neutralization pads which are sized and configured to engage the fractured metatarsal, at least a first of said compression pads sized and configured to engage a first side of the fractured metatarsal generally at said fracture site, and at least a second and a third of said compression pads being disposed in spaced apart relation from one another and being structured to engage a second side of the fractured metatarsal opposite said first side of the fractured metatarsal at points proximal and distal to said fracture site.

12. A metatarsal fracture neutralizer as recited in claim 1 further comprising a joint immobilization assembly coupled with at least one of said brace elements and structured to selectively limit a range of motion at an ankle of the foot and thereby limit an amount of weight that can be readily be placed on the foot.

13. A metatarsal fracture neutralizer as recited in claim 12 wherein said joint immobilization assembly includes an elongate, rigid panel extending from one of said brace elements along a bottom of the foot and into engaging relation with a heal of said foot, said rigid panel abutting said heal upon pivotal movement of a forward region of said away from said ankle, thereby limiting said range of motion.

14. A limb extremity fracture neutralizer comprising:

a first brace element and a second brace element, said first and said second brace elements being adjustably secured with one another in sandwiching relation about a limb extremity containing at least one fractured longitudinal bone;

a plurality of neutralization pads, said neutralization pads secured to said first and second brace elements in generally confronting relation with one another, said neutralization pads being structured to generally engage and immobilize the fractured longitudinal bone, said neutralization pads being further structured to generally engage and immobilize at least a second longitudinal bone disposed adjacent the fractured longitudinal bone so as to prevent movement of the fractured longitudinal bone as a result of muscle interconnection therebetween, said neutralization pads sized and configured to extend along a substantial length of the longitudinal bone and being structured and disposed to permit a substantial range of motion at joints connected to the longitudinal bones, thereby substantially aiding comprehensive rehabilitation of the limb extremity, at least two compression pads, said compression pads operatively coupled with at least said neutralization pads which engage the fractured longitudinal bone, at least one of said compression pads being structured and disposed to engage a first side of the fractured longitudinal bone at a fracture site, at least another of said compression pads being structured and disposed to engage a second side of the fractured longitudinal bone opposite the first side of the fractured longitudinal bone, said compression pad that is structured to engage the first side of the fractured longitudinal bone being structured to push the fractured longitudinal bone in a direction which opposes a direction of the fracture and which opposes a direction in which said compression pad that is structured to engage the second side of the fractured longitudinal bone pushes, thereby urging and maintaining the fractured longitudinal bone in an aligned, proper healing orientation, upon securement of said first and second brace elements with one another about the limb extremity, and each of said neutralization pads includes an elongate, generally narrow segment having a longitudinal trough defined therein wherein the longitudinal bone is received.

15. A limb extremity fracture neutralizer as recited in claim 14 wherein each of said neutralization pads further includes a lock channel defined in said longitudinal trough and structured to receive said compression pad therein, said compression pad including a lock segment that extends into said lock channel and includes an unlocked orientation wherein movement of said compression pad along said neutralization pad is permitted so as to achieve a desired positioning, and a locked orientation wherein said compression pad is secured in its position relative to said neutralization pad.

16. A limb extremity fracture neutralizer as recited in claim 14 further comprising a joint immobilization assembly coupled with at least one of said brace elements and structured to selectively limit a range of motion at a joint between extremity and a limb to which it is attached, and to thereby limit an amount of weight that can be readily be placed on the limb extremity.

17. A limb extremity fracture neutralizer comprising:

a first brace element and a second brace element, said first and said second brace elements being adjustably secured with one another in sandwiching relation about a limb extremity containing at least one fractured longitudinal bone;

a plurality of neutralization pads, said neutralization pads secured to said first and second brace elements in generally confronting relation with one another, said neutralization pads being structured to generally engage and immobilize the fractured longitudinal bone, said neutralization pads sized and configured to extend along a substantial length of the longitudinal bone and being structured and disposed to permit a substantial range of motion at joints connected to the longitudinal bones, thereby substantially aiding comprehensive rehabilitation of the limb extremity, at least three compression pads operatively coupled with at least said neutralization pads which are sized and configured to engage the fractured longitudinal bone, at least a first of said compression pads sized and configured to engage a first side of the fractured longitudinal bone generally at a fracture site, at least a second and third of said compression pads being disposed in spaced apart relation from one another and being structured to engage a second side of the fractured longitudinal bone opposite the first side of the fractured longitudinal bone at points proximal and distal to the fracture site, and said first compression pad and said second and third compression pads structured to generally push against one another, and to thereby urge and maintain the fractured longitudinal bone in an aligned, proper healing orientation, upon securement of said first and second brace elements with one another about the limb extremity.

18. A metatarsal fracture neutralizer comprising:

a first brace element and a second brace element, said first and said second brace elements being adjustably secured with one another and adapted to be in sandwiching relation about a foot containing at least one fractured metatarsal;

a plurality of neutralization pads, said neutralization pads secured to said first and second brace elements in generally confronting relation with one another, said neutralization pads being structured to generally isolate, engage and immobilize the fractured metatarsal, said neutralization pads being further structured to generally isolate, engage and immobilize at least a second metatarsal disposed adjacent the fractured metatarsal so as to prevent movement of the fractured metatarsal as a result of muscle interconnection therebetween, said neutralization pads being structured and disposed to permit a substantial range of motion at joints connected to the metatarsals of the foot, thereby substantially aiding comprehensive rehabilitation of the foot, at least three of compression pads adjustably and operatively coupled with at least said neutralization pads adapted to engage the fractured metatarsal, at least a first of said compression pads being disposed to engage a first side of the fractured metatarsal when in use generally at a fracture site, and at least a second and a third of said compression pads being disposed in spaced apart relation from one another and being structured to engage a second side of the fractured metatarsal opposite the first side of the fractured metatarsal at points proximal and distal to the fracture site.

19. A metatarsal fracture neutralizer as recited in claim 18 wherein said neutralization pads are adjustably secured to said brace elements so as to facilitate proper alignment with the metatarsals regardless of an actual spacing therebetween.

20. A metatarsal fracture neutralizer as recited in claim 18 wherein said neutralization pads extend along a substantial length of the metatarsals so as to maintain effective engagement therewith and isolation therebetween.

21. A metatarsal fracture neutralizer as recited in claim 18 further comprising a joint immobilization assembly coupled with at least one of said brace elements and structured to selectively limit a range of motion at an ankle of the foot and thereby limit an amount of weight that can be readily be placed on the foot.

* * * * *